US006605651B1

(12) United States Patent
Stangel et al.

(10) Patent No.: US 6,605,651 B1
(45) Date of Patent: Aug. 12, 2003

(54) CURING METHODS AND MATERIAL COMPOSITIONS HAVING DENTAL AND OTHER APPLICATIONS

(75) Inventors: Ivan Stangel, Bethesda, MD (US); Jingwei Xu, Montreal (CA)

(73) Assignee: Biomat Sciences, Inc., Rockville, MA (US)

(*) Notice: Subject to any disclaimer, the term of this patent is extended or adjusted under 35 U.S.C. 154(b) by 0 days.

(21) Appl. No.: 09/391,377

(22) Filed: Sep. 8, 1999

Related U.S. Application Data

(60) Provisional application No. 60/099,654, filed on Sep. 9, 1998.

(51) Int. Cl.$^7$ .................. A61K 6/083; A61K 6/093; A61K 6/087; C08J 3/28
(52) U.S. Cl. .................. 523/116; 523/105; 523/115; 523/117; 523/118; 522/81; 522/83; 522/96; 522/99; 522/103; 522/120; 522/121; 522/148; 522/182; 522/908
(58) Field of Search .................. 522/81, 83, 96, 522/99, 103, 120, 121, 148, 182, 908; 523/105, 115, 116, 117, 118

(56) References Cited

U.S. PATENT DOCUMENTS

| | | | |
|---|---|---|---|
| 4,527,560 A | | 7/1985 | Masreliez |
| 4,604,444 A | * | 8/1986 | Donnadieu et al. ............ 528/34 |
| 4,760,228 A | | 7/1988 | Kudo |
| 4,873,269 A | * | 10/1989 | Nakazato .................. 523/115 |
| 4,971,735 A | | 11/1990 | Uegayashi |
| 5,026,959 A | | 6/1991 | Ito et al. |
| 5,059,914 A | | 10/1991 | Lacombe et al. |
| 5,147,903 A | | 9/1992 | Podszum et al. |
| 5,151,279 A | | 9/1992 | Kimura et al. |
| 5,175,008 A | | 12/1992 | Ueno |
| 5,191,182 A | | 3/1993 | Gelorme et al. |
| 5,207,231 A | | 5/1993 | Fakhri |
| 5,218,070 A | | 6/1993 | Blackwell |
| 5,302,104 A | | 4/1994 | Ueda |
| 5,324,186 A | | 6/1994 | Bakanowski |
| 5,346,932 A | * | 9/1994 | Takahashi et al. .......... 523/213 |
| 5,358,515 A | | 10/1994 | Hürter et al. |
| 5,384,075 A | * | 1/1995 | Okami .................... 524/431 |
| 5,421,727 A | | 6/1995 | Stevens et al. |
| 5,456,603 A | | 10/1995 | Kowalyk et al. |
| 5,502,087 A | | 3/1996 | Tateosian et al. |
| 5,510,411 A | | 4/1996 | McKinstry et al. |
| 5,521,360 A | | 5/1996 | Johnson et al. |
| 5,632,955 A | | 5/1997 | Gabbai |
| 5,645,748 A | | 7/1997 | Schiffmann et al. |
| 5,648,038 A | | 7/1997 | Fathi et al. |
| 5,770,143 A | | 6/1998 | Hawley et al. |
| 5,893,713 A | | 4/1999 | Garman et al. |
| 6,033,401 A | | 3/2000 | Edwards et al. |
| 6,036,494 A | | 3/2000 | Cohen |
| 6,083,218 A | | 7/2000 | Chou |
| 6,103,779 A | * | 8/2000 | Guzauskas .................. 523/115 |
| 6,254,389 B1 | * | 7/2001 | Seghatol .................. 433/215 |
| 6,287,490 B2 | * | 9/2001 | Rheinberger et al. ....... 433/215 |
| 6,335,385 B2 | * | 1/2002 | Gorlich et al. .............. 523/115 |
| 6,441,354 B1 | | 8/2002 | Seghatol et al. |

FOREIGN PATENT DOCUMENTS

| | | |
|---|---|---|
| CA | 2120880 | 10/1995 |
| CA | 2148536 | 11/1995 |
| DE | 41 02 129 A1 | 7/1992 |
| EP | 0 193 514 B1 | 8/1990 |
| EP | 0 687 451 A2 | 12/1995 |
| JP | 63-296750 | 2/1988 |
| JP | 7-31632 | 2/1995 |

OTHER PUBLICATIONS

Urabe et al., "Influence of Polymerization Initiator For Base Monomer On Microwave Curing Of Composite Resin Inlays," Journal of Oral Rehabilitation 1999 26: 442–446.

Readers' Choice, "The Prosthoflex Automated Injection System From ATP Industries, Inc.," Dental Lab Product, Sep./Oct. 1995.

Hoshi et al., "Application of Microwaves and Millimeter Waves For The Characterization of Teeth For Dental Diagnosis and Treatment," IEEE Transactions on Microwave Theory and Techniques, vol. 46, No. 6, Jun. 1998.

Ferracane, "Elution Of Leachable Components From Composites," Journal of Oral Rehabilitation, 1994, vol. 24, pp. 441–452.

"Estrogenic Agents Leach From Dental Sealant," Science News, vol. 149, Apr. 6, 1996.

Hume et al., "Bioavailability of Components of Resin–Based Materials Which Are Applied To Teeth," Crit. Rev. Oral Biol. Med., 7(2):172–179 (1996).

Alkhatib et al., "Comparison of Microwave–Polymerized Denture Base Resins," The International Journal of Prosthodontics, vol. 3, No. 3, pp. 249–255, 1990.

Hayden, "Flexual Strength of Microwave–cured Denture Baseplates," General Dentistry/Sep.–Oct. 1986, pp. 367–371.

(List continued on next page.)

Primary Examiner—Peter Szekely
(74) Attorney, Agent, or Firm—Fitch, Even, Tabin & Flannery

(57) ABSTRACT

This invention provides a method and material compositions for producing objects containing in whole, or in part, biomedical polymers, especially those having dental use. Microwave sensitive material compositions are injected under pressure into a mold, the mold containing a replica of a body tissue or tissues. While hydraulic pressure is maintained on the material, a microwave source emits metered electromagnetic energy for hardening the material in the 3-dimensionally defined space. For dental and other applications, the mold making, injection and hardening are done sequentially to rapidly produce an object which accurately fits the mold.

25 Claims, 1 Drawing Sheet

OTHER PUBLICATIONS

Geerts et al., "A Comparison of the Bond Strengths of Microwave– and Water Bath–Cured Denture Material," The Journal of Prosthetic Dentistry, vol. 70, No. 5, pp. 406–409.

Turck et al., "Microwave Processing For Denture Relines, Repairs, And Rebases," The Journal of Prosthetic Dentistry, vol. 69, No. 3, pp. 340–343.

Doori et al., "A Comparison of Denture Base Acrylic Resins Polymerized By Microwave Irradiation And By Conventional Water Bath Curing Systems," Dent Mater 1988: 4: 25–32.

Salim et al., "The Dimensional Accuracy of Rectangular Acrylic Resin Specimens Cured by Three Denture Base Processing Methods," The Journal of Prosthetic Dentistry, Jun. 1992, vol. 67, No. 4, pp. 879–881.

Wallace et al., "Dimensional Accuracy of Denture Resin Cured By Microwave Energy," The Journal of Prosthetic Dentistry, Sep. 1991, vol. 66, No. 3, pp. 403–407.

Farrancane et al., "Wear And Marginal Breakdown of Composites With Various Degrees of Cure," J. Dent Res, 76(8), pp. 1508–1516 (Aug. 1997).

Feilzer et al., "Curing Contraction of Composites and Glass–Ionomer Cements," TheJournal of Prosthetic Dentistry, Mar. 1988, vol. 59, No. 3, pp. 297–300.

* cited by examiner

CURING METHODS AND MATERIAL COMPOSITIONS HAVING DENTAL AND OTHER APPLICATIONS

CROSS-REFERENCE APPLICATION

This application claims the priority benefit of provisional application 60/099,654 filed Sep. 9, 1998.

BACKGROUND OF THE INVENTION

Objects containing, or consisting of polymers are used in the dental arts for the replacement or restoration of lost tissue, for the improvement of oral function, for aesthetic enhancement, for the correction of tooth or jaw related problems, as well as other applications. They are required to have a precise fit, as well as certain physical, mechanical, chemical and biological properties. The objects need adequate strength, durability, processing accuracy and dimensional stability. They should be highly and appropriately polymerized to improve strength and stability, and they should be chemically inert so as not to constitute a biohazard. They additionally should be able to be processed rapidly and conveniently.

An example of a polymer object used in the dental arts is a composite resin. Most commercial composite resins consist of a resin matrix, an inorganic filler phase and some coupling agents. The resin matrix generally comprises a monomer system, an initiator system and other stabilizers. The monomer system consists of the unsaturated compounds. These compounds generally comprise one or more ester of ethylenically unsaturated carboxylic acids and the adduct of bisphenol A and glycidyl methacrylate, such as triethyleneglycol dimethacrylate (TEGDMA), ethyleneglycol dimethacrylate (EGDMA) and 2,2-bis-[4-(2-hydroxy-3-methacrylyloxypropoxy)phenyl]-propane ether (Bis-GMA) in U.S. Pat. No. 3,066,112 to Bowen. Another class of unsaturated material is urethane dimethacrylates, such as the 1,6-bis(methacrylyloxy-2-ethoxycarbonylamino-2,4,4-trimethylhexane (UEDMA) which is synthesized form 2-hydroxyethyl methacrylate and 2,4,4-trimethylhexamethylenediisocyanate.

The fillers include glasses, ceramics and inorganic oxides, which are generally the oxides of silicon, aluminum zirconium and other transition metals. Some surface treatments, such as silanization or with titanate, is normally employed before the use of the fillers. The fillers commonly have a particle size ranging from 0.04 to 100 microns, and constitute 50 to 80 weight percent of the composite.

Polymerization of these composite resins is usually achieved by free-radical polymerization using either chemical or photo-initiation. These two methods yield relatively incomplete conversion of the unsaturated compounds. The degree of conversion is generally in the 55–65% range. Incomplete conversion reduces the both mechanical and physical properties of the composite resins, and thus, clinical performance. In addition, unpolymerized monomer can be leached into saliva, and can become a biohazard. Thus, increasing the degree of conversion has benefits of improving the physical and mechanical properties of the composite, while improving the biocompatibility of the composite resin by reducing the leaching of uncured monomer.

The physical, mechanical and chemical properties of a composite include strength, stiffness, hardness, abrasion resistance, toughness, coefficient of thermal expansion, biocompatibility, and micro-shrinkage. Most properties are derived from all three basic components of the composite, although some are associated with one of the three constituents. Micro-shrinkage, one of the main shortcomings of composites, is primarily due to the resin matrix. The physical and mechanical properties, such as strength, hardness, stiffness and abrasion resistance, are highly influenced by resin matrix when the fillers and coupling agents are fixed.

Another disadvantage of dental polymers is that they shrink on hardening. This shrinkage compromises the fit, and, in the case of the composite resin, allows for leakage to occur between the composite and the tooth substrate. Although tooth adhesives can compensate somewhat for this shrinkage, bacterial and fluid leakage occurs between the composite and tooth interface, and can lead to diseases of the pulp (the vital organ contained within the central part of a tooth) and recurrent caries. Methods that improve the degree of conversion and reduce shrinkage would be very advantageous.

Improvements in the properties of polymer-containing materials can be obtained by using different processing methods. Composite cure can be enhanced by intensive visible-light exposure, as is done in the Triad device, (Denisply, USA) or by pressure and heat curing (Ivoclar, Schaan, Liechtenstein). These improvements still result in incomplete and less than satisfactory polymerization, as well as varying degrees of micro-shrinkage. Furthermore, improvements which substantially increase the degree of conversion generally require a laboratory step. Thus, in the dental arts, a highly precise replication of the body tissue is made, a replica is made, and an object is prepared using that replica. This requires two visits. The two visits and the laboratory procedure which can be costly constitute further disadvantages.

Microwave energy has a utility in the processing of polymers. Interest in microwave/radio frequency heating has increased over the last 30 years because of the continuous development of equipment capable of operating in an industrial environment. Conventional heating is concerned primarily with a relatively high-temperature heat source interacting with a relatively low-temperature product surface. In the absence of evaporation or other change of state, the rate of heating and temperature distribution from the surface inwards is governed by the thermal conductivities and specific heats of various constituents of a material. Usually, the rate of heating is slow, so that heat transfer by thermal conduction minimizes the temperature differences that would otherwise exist because of different specific heats; therefore, a relatively uniform temperature gradient from the warm surface to the cooler center of the material is found. In conventional heating, the usual thermal properties such as specific heat, thermal conductivity, coefficient of expansion and emissivity do not change significantly over the usual temperature range of the process.

The main advantages provided by microwave energy include: (1) good penetration, fast heating rates and shorter curing time, resulting in a reduction of the distortion; (2) minimal thermal lag and thermal gradients, which result in a more homogeneous cure and better mechanical properties.

Microwave curing of composites under pressure is one way of reducing polymerization shrinkage. Microwave curing of composites while injected into a mold further reduces porosity, and enhances density, and consequently improves the survival of the dental restoration.

Another problem caused by the residual monomers in the composite is the leaching of the unbound materials. The leaching has an impact on both the structural stability and biocompatibility. The residual monomers are eluted into salivary fluids and brought into contact with mucosal tissues; or be extracted into dentin and diffused to pulp. The elution decreases with the higher degree of conversion. An increase of degree of conversion will result in improved mechanical properties and biocompatibility of composite.

A further example of a polymer object is soft denture liners. Several kinds of soft denture liners are used, these being polysiloxane, polyurethanes, plasticized polymethacrylates, polyvinyl chlorides and polyphosphazene fluoroelastromers.

Most soft-liners have inherent disadvantages. These include the leaching of potentially harmful bonding agents, such as epoxy and urethane adhesives, sulfuric, perfluoroacetic acid; poor adhesion to the polymethylmethacrylate (PMMA) denture base due to the chemical dissimilarities between liners such as hydroxyl-terminated polydimethylsiloxane and PMMA; porosity in denture base and the liner resulting from vaporization of the solvent; dimensional changes caused by micro-shrinkage, or dehydration and rehydration steps.

The improvements of denture liners may be based on the use of novel materials, such as acryloxy or methacryloxy polydimethylsiloxanes and acryoxyalkyl or methacryloxyalkyl-terminated polydialkylsilozanes which have been recently introduced. Since these organosilicons have similarities with PMMA, the bonding between liners and the denture is improved, and use of bonding agents is avoided. However, the curing time for these liners, is relatively long.

Once hardened, on seating of the denture, the oral tissues are subjected to change and compression. A way to improve the fit of existing dentures is to, retake an impression, and have a denture rebased. This procedure is usually done in a laboratory, and the material characteristics are deficient in a manner similar to the materials that undergo water-bath hardening. In addition, the procedure takes two visits, is more time consuming, factors which add to the cost of the procedure. Chairside relines can be made using chemically-cured polymers, such as methylmethacrylates, polymethylmethacrylates, polyvinyl acrylates, 2,2-bis[(p-2'hydroxy-3'methacryloxy-propoxy)phenyl] propane, triethyleneglycol dimethacrylate, urethane dimethacrylate, or light-cured polymers. However, they have a relatively low degree of cure, are extremely porous since no compression is possible, and often can cause chemical and physical irritation of the oral tissues.

Problems existing in dental objects made of, or containing polymers may be caused by relatively incomplete degree of conversion, micro-shrinkage, and porosity. An increase in the degree of conversion, a decrease of micro-shrinkage, and a decrease in porosity will result in improved performance of these objects. Furthermore, a processing which more rapidly imparts improvements will have a greater utility for the dental profession. This can be achieved by microwave heating.

Microwave heating is uniquely different because heat is generated within the material rather than being generated externally. The dielectric properties that govern the rate of internal heating may vary widely in magnitude among various constituents of a multiphase, multi-component product. Furthermore, they may change very significantly with temperature. Therefore, the temperature distribution at a given time in a microwave/RF heated material will depend primarily on the dielectric properties, specific heats and thermal conductivity's of the material's constituents. The thermal conductivity's of the constituents may tend to equalize the local temperature variations, but often, the rate of heating with microwave energy is so high that internal conduction of heat cannot transfer the accumulated heat throughout the material.

The permittivity characteristics of polymers with or without filler at various frequencies and at various temperatures are published in the literature. Von Hippel presents a table of data at frequencies from 100 to 1010 Hz for various polymers and compounds. Ippen presents, in graphical form, the loss factors of various polymers, blends of polymers and polymers with various fillers as a function of temperature at 3 GHz. The selection of the proper frequency in microwave/RF heating is based on important parameter of the product of relative loss factor, $\epsilon''_r$ by frequency, f. The power absorption capacity of a material depends mainly on $\epsilon''_r$, f and its geometrical shape. Since the shape is variable, the only way to evaluate the heatability of materials is to examine the product $\epsilon''_r$ f.

SUMMARY OF THE INVENTION

It is an object of this invention to identify polymerizable microwave-sensitive compositions having primary use in the biomedical field, and in particular, in the dental arts, although the materials can be used elsewhere whenever rapid processing of precise shapes are required.

It is an object of this invention to introduce the compositions into a chamber, whereby hydraulic pressure is used to inject the material into a three-dimensional mold, the mold constituting a replica of a body part, and having an air escape vent.

It is an object of this invention to maintain pressure on the said compositions while the composition is in the mold.

It is an object of the present invention to harden the compositions using microwave energy, delivered to the mold which is contained in a microwave chamber.

It is an object of this invention to perform an in situ (directly in the mouth) hardening of the said polymerizable composition used for the restoration of teeth using a hand-held apparatus placed in the vicinity of the composition, which has been placed in a tooth.

DETAILED DESCRIPTION OF THE INVENTION

Figure 1A:
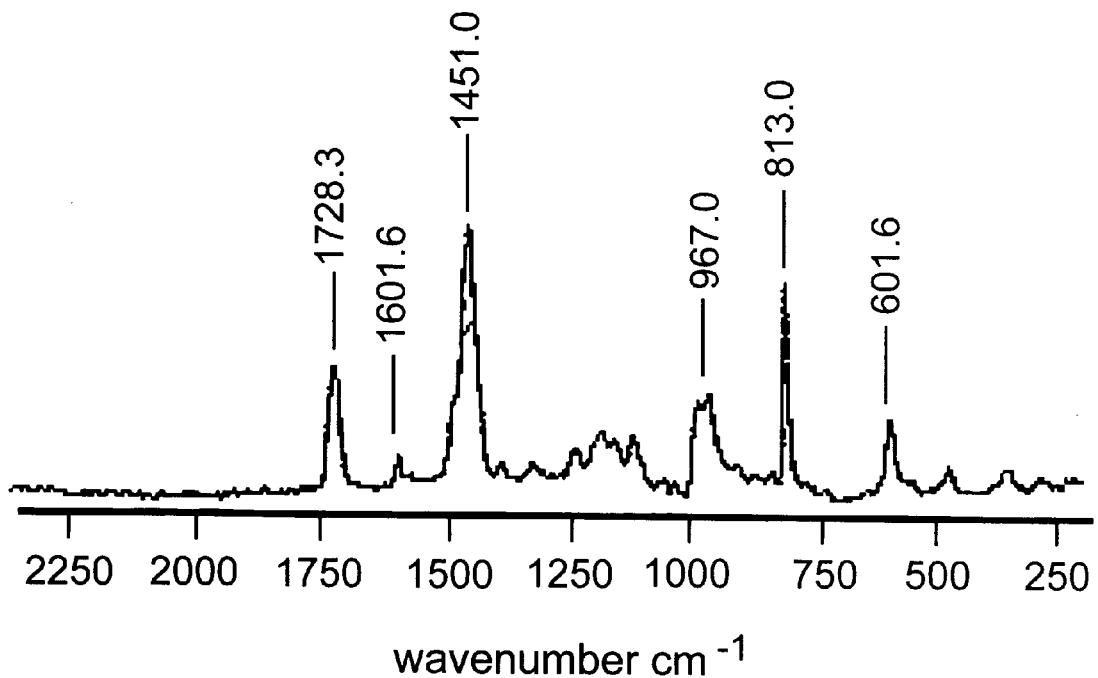
FIG. 1(a) and FIG. 1(b) are FT-Raman Spectra of uncured and cured polymethylmethacrylate, respectively.

In dental arts, various compositions are useful for the construction of dental devices containing polymers in part, or in whole. These compositions may be used in the filling of teeth and the construction of appliances used for replacing teeth and other oral structures. One utility of these compositions is in the restoration of lost tooth tissue, while another is in the construction of removable dental appliances including (such as dentures, soft and hard relines). The compositions in this invention are also useful for the construction and forming of composite fillings crowns, bridges, inlays, onlays, temporary prostheses, inlays or onlays, facings, veneers, orthodontic appliances.

A preferred composition for a dental composite adapted to cure with the method and apparatus of this invention include: (I) polymerizable resin suitable for use in the oral environment, which comprise 2,2-bis[4-(2-hydroxy-3-methacrylyloxypropoxy)phenyl]propane (BisGMA) (ratio), ethyleneglycol dimethacrylate (EGDMA) and triethyleneglycol dimethacrylate (TEGDMA), eutectic monomers, hydrophobic (hydrophilic) monomers, urethane dimethacrylate resins, spiro orthocarbonates, organo-esters of phosphorus: (II) inorganic or organic fillers: (III) coupling agents and other additives.

A preferred embodiment of the composition for a dental composite according to the present invention consists of (I) a polymerizable resin suitable for use in the oral environment, which includes 2,2-bis[4-(2-hydroxy-3-methacrylyloxypropoxy)phenyl]propane (BisGMA), ethyleneglycol dimethacrylate (EGDMA) and triethyleneglycol dimethacrylate (TEGDMA), urethane dimethacrylate, eutectic monomers, hydrophobic monomers, urethane dimethacrylate resins, spiro orthocarbonates, organo-esters of phosphorous: (II) inorganic or organic fillers described; (III) polyfunctional coupling agents, such as gamma-methoxypropylene silane, or a silane-containing coupler which can form siloxane linkages with inorganic particles and co-polymerizes with a polymer matrix, or an alkylthiol having a methacrylate functionality, such that the thiol end forms a self assembled monolayer on the metal particles, and the methacrylate functionality co-polymerizes with a polymer matrix; and other additives. The weight % of the organic filler as an overall weight of the composite can be in the range of 30 to 96%, but preferably is in the range of 50 to 75%.

The composite contains organic peroxide microwave sensitive polymerization initiators. The organic peroxide in accordance with this invention can be benzoyl peroxide, dilauroyl peroxide, tert-butyl peroctoate, tert-butyl perbenzoate, 2,4-dichlorobenzoyl peroxide or 4,4-dichlorobenzoyl peroxide in the weight range of 0.05% to 1.0% in the composition, preferably in the range of 0.09 to 0.5%, and amine accelerators, such as N,N-diethenol-p-toluidine, or triethylamine.

The polymerizable resin combinations include Bis-GMA and TEGDMA, and can have a mixture ratio of 0.3 to 0.7, preferably in the range of 0.5, and is suitable to the method and apparatus disclosed in this invention by the use of provided microwave sensitive polymerization initiators for making and using the curable material system. Urethane dimethacrylate can be substituted for TEGDMA.

The inorganic filler particles in accordance with the invention comprise (silica) calcium, strontium, lanthanum, barium, rare earth, alumina, silicate in crystalline, or in aluminosilicate with a zeolite structure, and fluoride of the rare earth metals or mixtures of such fluorides (glass pyrogenicaly produced, ceramics, zirconium. They comprise particle sizes ranging from 0.04 micrometers to approximately 10 micrometers, preferably being distributed between 1 and 7 micrometers. Composites can also exclusively contain submicron colloidal silica, or pre-polymerized polymer containing colloidal silica having particles. They can also contain metal particles having sizes ranging from 0.04 micrometers to approximately 10 micrometers, preferably being distributed between 1 and 7 micrometers. The metal particles can be pure gold, or silver, or alloys of silver and tin, which may be surface-modified with a coating of pure silver or pure gold.

Compositions are provided and which are especially suitable for removable dental prostheses comprise a liquid component (i) and a powdery component (ii). The liquid component in accordance with the invention contains from (20% to 98%) more preferably (30% to 95%), most preferably (40% to 90%) of mono-, di-, tri-, or multifunctional acrylic monomer. The liquid component in accordance with the invention includes advantageously a plasticizer, an accelerator and a cross-linking agent.

The mono-, di, tri, or multifunctional acrylic monomer in accordance with the present invention are within the scope of the general formula (I)

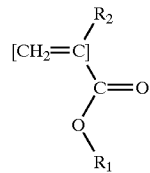

wherein $R_1$ represents hydrogen, alkyl, substituted alkyl group, cyclic hydrocarbon, benzyl, ether, hydroxyalkyl; and $R_2$ represents hydrogen, halogen, alkyl, substituted alkyl or cyclic hydrocarbon group. These monomers may be used alone or in admixture.

In accordance with this invention, a microwave sensitive initiator system can be peroxide such as benzoyl peroxide, dilauroyl peroxide, tert-butyl peroctoate or tert-butyl perbenzoate, 2,4-dichlorobenzoyl peroxide and 4,4-dichlorobenzoyl peroxide. The cure accelerator in accordance with the present invention is a quaternary ammonium chloride, which is easily soluble in the methacrylate monomers and reacts with barbituric acid derivatives. The preferable compounds are quaternary ammonium halides with alkyl of 1 to 20 carbon atoms, such as, dodecyltrimethylammonium chloride, dimethyldioctadecylammonium bromide, or dioctyldimethylammonium chloride. These quaternary ammonium chlorides may be added alone or in admixture.

The crosslinking agent in accordance with the provided microwave curable material composition is a polyfunctional monomer wherein at least two carbon-carbon double bonds, such as 1,3-butanediol dimethacrylate, 1,4-butanediol dimethacrylate, 1,4-butanediol divinyl ether, di(ethylene glycol) dimethacrylate, di(ethylene glycol) divinyl ether, pentaerythritol diacrylate monostearate, ethylene glycol dimethacrylate, trimetylolpropane trimethacrylate, pentaerythritol triacrylate, pentaerythritol triallyl ether, pentaerythritol tetraacrylate, trimetylolpropane triacrylate. The crosslinking agent may be used along or in admixture.

A cure promoter for the monomers of the provided curable material system (such as acrylates) is needed. When these compositions are irradiated with microwaves, barbituric acid derivatives rapidly react with the quaternary ammonium chloride to produce radicals, which promotes a rapid and uniform polymerization in the composition and a higher degree of conversion. The barbituric acid derivative in accordance with the invention include 1,3,5-trimethylbarbituric acid, 1,3-dimethyl-5-isobutylbarbituric acid, 1,3-dimethyl-5-phenylbarbituric acid, 5-n-butylbarbituric acid, 5-ethylbarbituric acid, 5-phenylbarbituric acid, 1-cyclohexyl-5-ethylbarbituric acid and 1-benzyl-5-phenylbarbituric acid. These acid derivatives may be used alone or in admixture an admixture.

A polymerization inhibitor, such as hydroquinone, 4-ethoxyphenol, 2-hydroxy-4-methoxybenzophenone, may be added to the liquid to keep the storage stability up to three years. The plasticizer in accordance with the invention is generally a low molecular weight ester, such as dibutyl phthalate or phosphates.

The composition for a one component microwavable curable denture base in accordance with this invention is approximately the same as the one for the two component materials with some variations mainly in the initiation system. Preferred initiators used in one component denture base are be thermally stable at room or higher temperatures such as 60 degree C. and initiate polymerization at temperatures higher. Suitable initiators include benzopinacole, tert-butylp erbenzoate, and tert-butylperisononanoate (ratio, temperature).

The powder component in accordance with the invention includes from (15% to 90%) more preferably (30% to 75%), [most preferably (45 to 70%)] (by weight) or mono-di-tri, or multifunctional acrylic or acrylate ester polymer. The powder may advantageously include from (0% to 70%), preferably (1.5% to 60%), most preferably (3% to 40%) of a copolymer. The powder component in accordance with the invention may advantageously include (0% to 15%), more preferably (0.1% to 10%), most preferably (0.1% to 5%) (and 0.1% to 3%) of an initiator (for radical polymerization) such as organic peroxide. The powder component in accordance with the invention can include up to (5%), preferably up to (3%), more preferably up to 1% of a barbituric acid derivative (to promote chemical reaction).

The mono-, di, tri, or multifunctional acrylic polymers used in the denture according to the present invention have a molecular weight of at least 143 and are within the scope of the general structural formula (II):

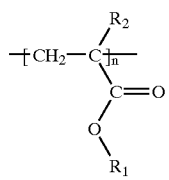

wherein $R_1$ represents hydrogen, an alkyl group, a substituted alkyl group, cyclic hydrocarbon, benzyl, ether, hydroxyalkyl; $R_2$ represents hydrogen, halogen, an alkyl group, a substituted alkyl group; and n is an integer at least equal to 2.

In accordance with this invention, the polymer is composed mainly of a methyl methacrylate polymer or a mixture of methyl methacrylate polymer and a methacrylate polymer other than methyl methacrylate polymer with the general formula (II), wherein $R_1$ is neither hydrogen or methyl. Inorganic and organic fillers may be added into the compositions of one or two component denture base.

Useful inorganic fillers include glass, metal ceramics, silicon in powdery or fiber format, which are preferably silaned with coupling agent such as 3-methacryloxloxypropyltrimethoxy silane by the common techniques used in dental science. Organic fillers include splinter or bead polymers of high molecular weight, or fibers such as carbon fibers, aramide fibers, polyethylene fibers, polyacrylate fibers, polyester fibers, polyamide fibers and polyacrylonitrile fibers. Organic fillers may be used along or mixed with inorganic fillers.

Soft material composition for applications such as denture liners formed and cured with the provided novel method include one and two component compositions: (I) an amount of one or more organopolysiloxanes, preferably methacryloxypropyl-terminated polydimethyl siloxanes, a crosslinking agent which contains at least two functional groups and an initiator and (II) an amount of a phosphonitrilic fluoroelastomer [poly(fluroalkoxy)phosphazene], [a crosslinking agent which contains at least two functional groups, a filler and an initiator].

Organopolysiloxanes and phosphonitrilic fluoroelastomers are particularly suitable as microwave-curable soft material systems with the method provided in this invention.

(With the exception the high degree of thermal and oxidative stability, low degree of toxicity and high chemical inertness, organosilicon is very resilient as a result of the motions of Si—O—Si and Si—C bonds in the main and side chains). The organopolysiloxanes in the compositions for soft denture liners in accordance with the invention are within the scope of the general structural formula (III):

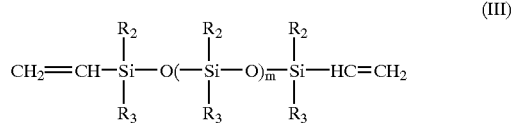

Form (IV)

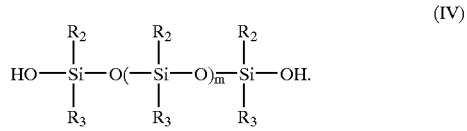

Wherein m is an integer having a value form 1 to about 6,000; n is an integer having a value form 1 to 6; R1 is hydrogen or alkyl group, R2 and R3 are alkyl groups having 1 to 6 carbons. The most preferred polysiloxanes is the methacryloxy-terminated polydimethylsiloxames with the structure (V). The adhesion of methacryloxy-terminated polydimethylsiloxanes to PMMA is improved due to the chemical similarity between these two materials.

Form V:

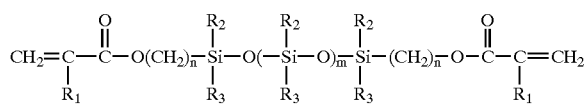

The crosslinking agent in accordance with the invention may be used in the soft denture liners. The crosslinking agents are normal multifunctional monomers that have at least two carbon-carbon double bonds. The most preferred crosslinking agents monomers, are acryloxy or methacryloxyalkyl-terminated siloxane monomers, such as 1,3-bis[p-acryloxymethyl] phenethyl] tetramethyldisiloxane, 1,3-bis(3-methacryloxypropyl) tetramethyldisiloxane (MPTDS), due to the similarity between crosslinking agent and organopolysiloxanes.

The initiators in the soft denture liners in accordance with the invention are general peroxides, such as benzoyl peroxide, lauroyl peroxide, tert-butyl peroctoate or tert-butyl perbenzoate.

Phosphonitrile fluoroelastomers in accordance with this invention are obtainable by polymerizing monomers with the general formula (VI):

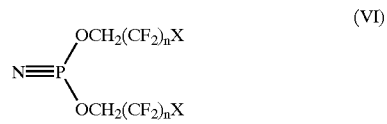

wherein X is H or F, and n is usually from 1 to 11. This material is commercially available as EYPEL-F:

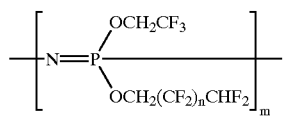

wherein n is 3, 5, 7, 9, or 11, and m is from 10,000 to 50,000. In order to minimize the absorption of water the NaCl contained in the EYPEL-F should be moved out prior to by extraction and coagulation from acetone.

The crosslinking agent suitable for the fluoroelastomers is the monomers with at least two functional groups, such as tetraethylene glycol dimethacrylate (TEGDMA), ethylene glycol dimethacrylate (EGDMA), 1,6-hexamethylene glycol dimethacrylate (HGDMA), trimethylolpropane trimethacrylate (TMP-TMA), pentaerythritol triacrylate, pentaerythritol triallyl ether, pentaerythritol tetraacrylate.

The fillers, improve hardness and the ability to grind and polish the cured fluoroelastomer and the bond strength between the liner and base due to the chemical similarity between filler and denture base. Particles of fillers may be beads or fibers [for example the fillers from a hard, grafted PMMA] pigments and other additives can be advantageously incorporated to material system.

Thermoplastic compounds such as acrylates and poly functional methacrylate, polycarbonate, polysulfone, superplastic, fluoropolymers, nylons, alloys, polimides, elastomers, polyester carbonates, polyurethanes, impression compound and shellac, wax, polycaprolactone and mixture of thermosets and thermoplastics can be advantageously processed and utilized with the provided method to assist dental rehabilitation therapies.

Microwave absorbing substances can advantageously be incorporated into disclosed thermoplastic and thermohardening material compositions. This is useful to characterize energy absorbency of materials to be processed where the employed material does not have sufficient dielectrical loss at the delivered microwave frequency nor does it have sufficient heatability for a given and desired speed of heating. These □absorbents□ are also useful when the employed material has a low microwave absorption behavior at low temperatures such as many thermoplastic polymers including polycarbonate or for substantially increasing the speed and adressability such as in welding functions. These substances may be powders, hollowed, coated; they may also be in a liquid, gaseous, or solid state and include ferromagnetics, metallic oxides and speciality ceramics.

These microwave absorbents generate and dissipate heat and infrared energy under microwave irradiation.

The materials described herein can be used with any suitable microwave device. In one embodiment of this invention, the device is a three dimensional object having an opening on one side, the opening being sealed by a door suspended by hinges, and having a locking mechanism. The object is made from materials which are impenetrable to the microwave energy, and which internally reflect the microwaves. A microwave-emitting source is located within the object, at the top. A receiving chamber is contained in the object, into which a polymerizable material is placed, and which is made of a material which shields the polymerizable material from the microwave energy. A pressurizing mechanism consisting of compressed air, or a hydraulic mechanism, and a piston injects the polymerizable material from the chamber into the mold via a short, hollow rod. The rod, having an internal bore, measures from 1 to 30 millimeters in length, and the bore has a diameter measuring from 3 to 30 millimeters in diameter. The length and diameter of the bore are determined by the nature of the polymerizable material to be injected. The rod is made of materials which are impenetrable to microwave energy. A mold, which made of a microwave transparent material, is connected to the rod via a coupler, the coupler tightly binding the mold to the rod, and which is capable of being rotated by a gearing system connected to an electric motor. A small diameter air escape valve is connected to the mold.

The polymerizable material is placed into the receiving chamber, and is injected into the mold, until the mold is overfilled with material, and the material is kept under pressure. At this time, the material is hardened by the microwave energy, while the mold is rotating. The time of exposure will vary from 1 to 50 minutes, this being dependent on the size and particular composition of the object.

In a preferred embodiment for the fabrication of composite resin inlays and crown for the restoration of teeth, a hand-held reduced size microwave emitting device is brought to the tooth to expose a composite resin formulation that has been placed in the tooth. The frequencies emitted can be 2.45 GHz, or preferably, or at 15,18,22,28 GHz. The optimal frequency will be determined by the permitivity of the polymerizable composition being used.

It should be understood that while the present invention has been described in considerable detail with respect to certain specific embodiments thereof. However, it should not be considered limited to such embodiments but may be used in other ways without departure from the intent of the invention and the scope of the claims.

EXAMPLE 1

The effect of microwave curing on dental polymers was measured. Bars conforming to the ISO standard for measuring flexural strength were made using a resin mixture consisting of BIS-GMA:TEGDMA at a 1:1 ratio. Bars were either cured chemically (n=4), by visible light (n=5), or microwave energy (n=4). Cured samples were subjected to a three-point bend test, and flexural strength calculated. The mean values in MP3 and (standard deviations) for each of the samples respectively were 18.5 (4.4), 45.9 (7.3), and 59.0 (6.9). Analysis of the means by a one-way ANOVA gave a p value <0.001. Post-hoc comparisons using Tukey's method indicated that differences between all groups were significant (p<0.05), and that the microwave cure significantly increased.

EXAMPLE 2

Figure 1B:
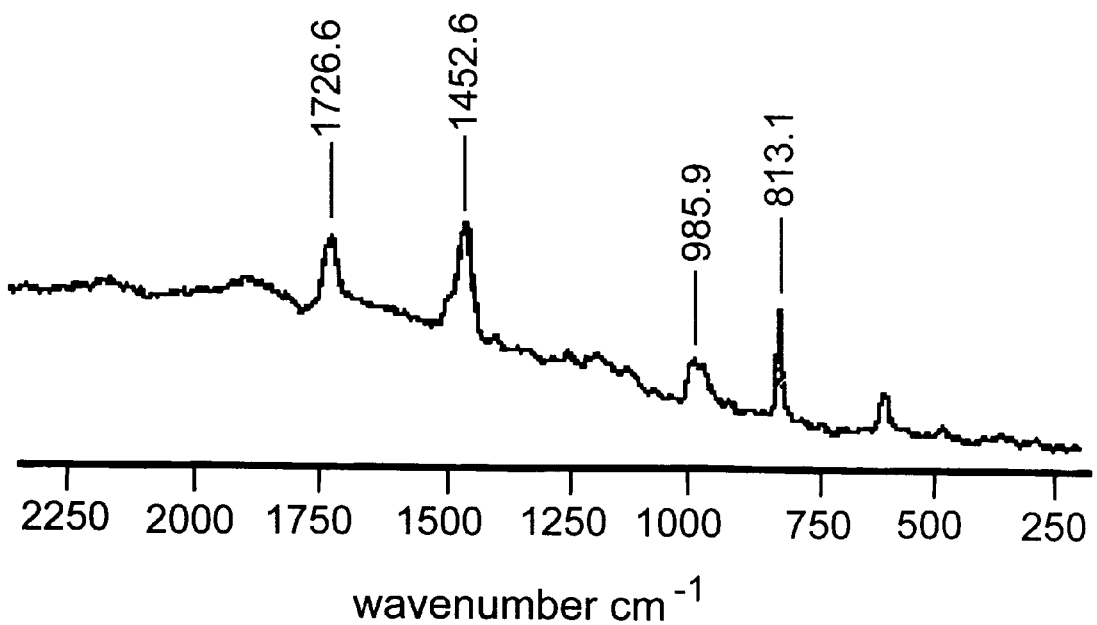

To evaluate the effect of microwave curing on the degree of conversion of a microwave sensitive composition consisting of polymethylmethacrylate (PMMA), spectra of uncured and cured PMMA (FIGS. 1(*a*) and 1(*b*)) were recorded using FT-Raman spectroscopy. The C═C peak (the unsaturated carbons) is observed at 1602 cm-1 in the uncured sample in 1(*1*). The peak virtually disappears in the cured sample 1(*b*), indicating that the degree of conversion is nearly complete. The degree of conversion is calculated by the method described in Ferracane, and was determined to be 92%.

We claim:

1. A method for reconstructing a part of a tooth using a hardened object, said method comprising
   (i) forming a hardenable object into a shape suited for reconstructing part of a tooth from a microwave curable composition comprising
      (a) multi-functional polymers and monomers at least one member selected from the group consisting of a mono-functional methacrylate polymer, di-functional methacrylate polymer, tri-functional methacrylate polymer, mono-functional methacrylate monomer, di-functional methacrylate monomer, and tri-functional methacrylate monomer; filler; coupling agent; initiator; plasticizer; and optionally additional additives for pigmenting; or (c) a polymer matrix including a polymerizable resin adapted for use in an oral environment which contains at least one ester of unsaturated compounds; coupling agent; filler, initiator; and; optionally, additional additives for pigmenting; and (ii) using a hand held microwave source to apply microwave energy to harden said hardenable object.

2. A method for forming a hardened reline material for a dental prosthesis comprising forming a hardenable object configured for relining a dental prosthesis from a microwave curable composition comprising a polymer matrix including a polymerizable resin adapted for use in an oral environment which contains at least one of 2,2-bis[4-(2-hydroxy-3-methacrylyloxpropoxy) phenyl]propane, ethyleneglycol dimethacrylate, triethyleneglycol dimethacrylate, or an urethane dimethacrylate resin; filler; initiator; coupling agent; and optionally, additional additives for pigmenting; and (ii) using a hand held microwave source to apply microwave energy to harden said hardenable object.

3. A method for forming a hardened object comprising
(i) forming a hardenable object from a microwave curable composition comprising
(a) at least one polymer including repeating monomer units represented by the formula (I)

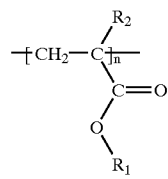

wherein
$R_1$ represents a hydrogen atom, an alkyl group, a substituted alkyl group, a benzyl group, a hydroxy alkyl group, a cyclic hydrocarbon, or an ether group,
$R_2$ represents a hydrogen atom, a halogen atom, an alkyl group, or a substituted alkyl group, and
n is an integer of two or more;
a curing agent; a filler; an initiator; a plasticizer; and optionally additional additives for pigmenting;

(b) at least one member selected from the group consisting of an organopolysiloxane and a phosphonitrile fluoroelastomer; filler; crosslinking agent; and, optionally additional additives for pigmenting; or (c) a polymer matrix including a polymerizable resin adapted for use in an oral environment which contains at least one of 2,2-bis[4-(2-hydroxy-3-methacrylyloxypropoxy) phenyl]propane, ethyleneglycol dimethacrylate, triethyleneglycol dimethacrylate, or an urethane dimethacrylate resin; filler; initiator; coupling agent and, optionally, additional additives for pigmenting; and (ii) using a hand held microwave source to apply microwave energy to harden said hardenable object.

4. A method for forming a hardened object comprising
(i) forming a hardenable object from a microwave curable composition, said object when cured comprising a dental prosthesis or an orthopedic element, said microwave curable composition comprising
(a) at least one member selected from the group consisting of mono-functional methacrylate polymer, di-functional methacrylate polymer, tri-functional methacrylate polymer, mono-functional methacrylate monomer, di-functional methacrylate monomer, and tri-functional methacrylate monomer; curing agent; filler; initiator; plasticizer; and optionally additional additives for pigmenting;

(b) at least one member selected from the group consisting of an organopolysiloxane and a phosphonitrile fluoroelastomer; filler; crosslinking agent; and, optionally additional additives for pigmenting; or (c) a polymer matrix including a polymerizable resin adapted for use in an oral environment which contains at least one of 2,2-bis[4-(2-hydroxy-3-methacrylyloxpropoxy) phenyl]propane, ethyleneglycol dimethacrylate, triethyleneglycol dimethacrylate, or an urethane dimethacrylate resin; filler; initiator; coupling agent; and; optionally, additional additives for pigmenting; and (ii) using a hand held microwave source to apply microwave energy to harden said hardenable object.

5. A method according to claim 1, wherein (c) comprises a polymer matrix including a polymerizable resin adapted for use in an oral environment which comprises at least one of 2,2-bis[4-(2-hydroxy-3-methacrylyloxypropoxy) phenyl]propane, ethyleneglycol dimethacrylate, triethyleneglycol dimethacrylate, or an urethane dimethacrylate resin; filler; initiator; coupling agent; and, optionally, additional additives for pigmenting.

6. A method according to claim 1, wherein said composition is (a).

7. A method according to claim 1, wherein said filler comprises inorganic filler or organic filler.

8. A method according to claim 1, wherein said filler comprises inorganic filler having particle sizes in the range of 0.4 micrometers to approximately 10 micrometers.

9. A method according to claim 1, wherein said filler comprises inorganic filler having particle sizes distributed in the range of 1 to 7 micrometers.

10. A method according to claim 3, wherein said at least one phosphonitrile fluoropolymer
is obtained by polymerizing monomers comprising:

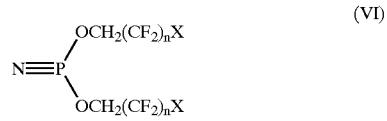

wherein X represents a hydrogen atom or fluorine atom, n is a value of 1 to 11; or has repeating monomer units represented by formula (VII):

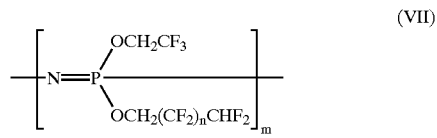

wherein n represents 3, 5, 7, 9 or 11 and m is from 10,000 to 50,000.

11. A method according to claim 3, wherein said organopolysiloxane is represented by any of the formulas (III), (IV) or (V)

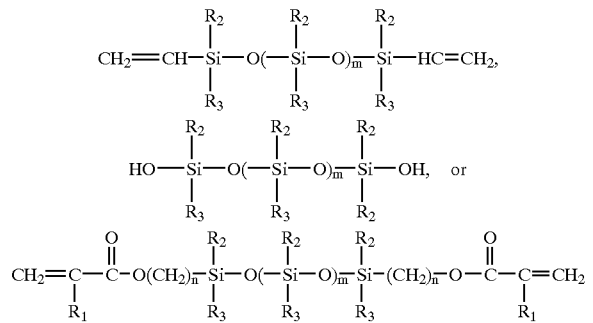

wherein said formulas m represents a value of 1 to about 6,000, n represents an integer having a value of 1 to 6, $R_1$ represents a hydrogen atom or an alkyl group, $R_2$ represents an alkyl group of 1–6 carbon atoms, and $R_3$ represents an alkyl group having 1–6 carbon atoms.

12. A method according to claim 4, wherein said hardened object comprises a dental prosthesis.

13. A method according to claim 12, wherein said dental prosthesis comprises a composite resin filling, inlay, overlay, facing, veneer or orthodontic appliance.

14. A method according to claim 4, wherein said filler comprises inorganic or organic filler.

15. A method according to claim 4, wherein said filler comprises inorganic filler having particle sizes in the range of 0.4 micrometers to approximately 10 micrometers.

16. A method according to claim 4, wherein said filler comprises inorganic filler having particle sizes distributed in the range of 1 to 7 micrometers.

17. A method according to claim 2, wherein said filler comprises inorganic filler or organic filler.

18. A method according to claim 2, wherein said filler comprises inorganic filler having particle sizes in the range of 0.4 micrometers to approximately 10 micrometers.

19. A method according to claim 2, wherein said filler comprises inorganic filler having particle sizes distributed in the range of 1 to 7 micrometers.

20. A method according to claim 1, wherein said composition comprises (c).

21. A method according to claim 20, wherein said initiator comprises at least one microwave sensitive compound.

22. A method according to claim 21, wherein said initiator comprises at least one member selected from the group consisting of benzoyl peroxide, dilauroyl peroxide, (tert-butyl) peroctoate, tert-butyl perbenzoate, 2,4-dichlorobenzoyl peroxide and 4,4-dichlorobenzoyl peroxide.

23. A method according to claim 21, wherein said composition contains 0.05% to 1.0% by weight of said initiator.

24. A method according to claim 20, wherein said coupler comprises gamma-methoxypropylene silane or a thiomethacrylate.

25. A method according to claim 1, wherein (a) further comprises an amine accelerator.

* * * * *